(12) United States Patent
Hauser et al.

(10) Patent No.: US 8,727,609 B2
(45) Date of Patent: May 20, 2014

(54) METHOD FOR THE THERMAL CHARACTERIZATION OF A PORTION OF MATERIAL

(75) Inventors: David Hauser, Paris (FR); Marc Plissonnier, Eybens (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 93 days.

(21) Appl. No.: 13/502,921

(22) PCT Filed: Oct. 28, 2010

(86) PCT No.: PCT/EP2010/066326
§ 371 (c)(1),
(2), (4) Date: Apr. 30, 2012

(87) PCT Pub. No.: WO2011/051376
PCT Pub. Date: May 5, 2011

(65) Prior Publication Data
US 2012/0207188 A1     Aug. 16, 2012

(30) Foreign Application Priority Data

Oct. 30, 2009 (FR) ..................... 09 57697

(51) Int. Cl.
*G01N 25/18* (2006.01)
*G01K 7/00* (2006.01)
*G01K 13/00* (2006.01)

(52) U.S. Cl.
USPC ............................. 374/44; 374/183; 374/141

(58) Field of Classification Search
CPC ..... G01N 25/005; G01N 25/18; G01N 27/72; G01K 17/006; G03F 7/70708

USPC ........................................... 374/44, 183, 141
See application file for complete search history.

(56) References Cited

U.S. PATENT DOCUMENTS 5,044,766 A * 9/1991 Stuart ........................... 374/43
5,080,495 A   1/1992 Hashimoto et al.

FOREIGN PATENT DOCUMENTS

DE          44 10 315 A1   11/1995
DE   10 2004 022 206 A1   12/2005
JP           60173449 A *    9/1985

OTHER PUBLICATIONS

French Preliminary Search Report Issued May 27, 2010 in Patent Application No. FR 0957697 (with English Translation of Categories of cited Documents).

(Continued)

*Primary Examiner* — Mirellys Jagan
(74) *Attorney, Agent, or Firm* — Oblon, Spivak, McClelland, Maier & Neustadt, L.L.P.

(57) ABSTRACT

A method for thermal characterization of a portion of first material of elongate shape on which there is arranged a portion of a second, electrically conductive material of elongate shape, the method including: a) determining characteristic of the portion of second material, b) applying an electric current of angular frequency between ends of the portion of the second material, and measuring the angular frequency harmonic of the electric voltage between these ends for different values of angular frequency, c) calculating coefficient of thermal conductivity of the portion of first material from the values of the harmonic and of the determined characteristic, a width of the portion of the first material being between about 0.9 and 1.1 times the width of the portion of second material, the portion of first material being surrounded by thermal insulation.

12 Claims, 2 Drawing Sheets

(56) References Cited

OTHER PUBLICATIONS

Brandon W. Olson et al., "A practical extension of the 3ω method to multilayer structures", American Institute of Physics, XP012079385, vol. 76, No. 5, 2005, pp. 053901-1-053901-7.

T. Borca-Tasciuc et al., "Data reduction in 3ω method for thin-film thermal conductivity determination", American Institute of Physics, XP012039099, vol. 72, No. 4, Apr. 2001, pp. 2139-2147.

Tsuneyuki Yamane et al., "Measurement of thermal conductivity of silicon dioxide thin films using a 3ω method", American Institute of Physics, XP002561390, vol. 91, No. 12, Jun. 15, 2002, pp. 9772-9776.

David G. Cahill, "Thermal conductivity measurement from 30 to 750 K: the 3ω method", American Institute of Physics, vol. 61, No. 2, Feb. 1990, pp. 802-808.

David G. Cahill et al., "Thermal conductivity of α-Si:H thin films", The American Physical Society, vol. 50, No. 9, Sep. 1, 1994, 6 pages.

David G. Cahill et al., "Thermal conductivity of amorphous solids above the plateau", The American Physical Society, vol. 35, No. 8, Mar. 15, 1987, pp. 4067-4073.

David G. Cahill et al., "Thermal conductivity of thin films: Measurements and understanding", American Vacuum Society, vol. 7, No. 3, May/Jun. 1989, pp. 1259-1266.

A. Delan et al., "Thermal Conductivity Measurement of Thin Dielectric Films Using the 3ω Technique", 2002, pp. 49-50.

\* cited by examiner

METHOD FOR THE THERMAL CHARACTERIZATION OF A PORTION OF MATERIAL

TECHNICAL FIELD

The invention concerns the field relating to the thermal characterization of materials, and more particularly a method for the thermal characterization of a portion of material allowing the thermal conductivity of this portion of material to be determined.

STATE OF THE PRIOR ART

The 3ω method allows the thermal characterization of the layers of materials by determining thermal conductivity of these layers. This method is described in the document <<Thermal conductivity of amorphous solids above the plateau>> by D. G. Cahill and R. O. Pohl, Physical Review B, vol. 35, March 1987, page 4067.

According to the 3ω method, when it is desired to measure the thermal conductivity of a thin layer of material, a test structure is prepared such as the one illustrated in FIG. 1 comprising a microwire 4 composed of a metallic material of width 2b (b corresponding to one half of the width of the microwire), forming a metal line deposited on a layer of material 8, called a sample, whose thermal conductivity it is sought to measure. This sample is itself arranged on a substrate 2.

When implementing the 3ω method, first the TCR (Temperature Coefficient of Resistance) of the metal line 4 is measured. This measurement comprises placing the test structure on a heating substrate and measuring the electric resistance R of the metal line 4 in relation to the different temperatures T to which the test structure is subjected.

The characteristic R(T) obtained is adjusted by a second-degree polynomial to calculate the Temperature Coefficient of Resistance $\alpha_R$ of the metal line 4 such that:

$$\alpha_R = \frac{1}{R} \cdot \frac{dR(T)}{dT} \quad (1)$$

At a second step, a sinusoidal electric current i(t) of angular frequency ω and amplitude $I_0$ is caused to circulate in the metal line 4.

This current then generates heating by Joule effect of angular frequency 2ω whose power p(t) can be written as:

$$p(t) = \frac{I_0^2 \cdot R}{2} \cdot (1 + \cos(2\omega t)) \quad (2)$$

This heating leads to a temperature variation ΔT in the metal line 4 at frequency 2ω such that:

$$\Delta T = \Delta T_0 \cdot \cos(2\omega/+\phi) \quad (3)$$

Yet, this temperature variation ΔT also leads to a variation at 2ω of the electric resistance R of the metal line 4, such that:

$$R(T) = R_0 \cdot [1 + \alpha_R \cdot \Delta T] \quad (4)$$

The 3ω harmonic is then measured of the voltage at the terminals of the metal line 4, denoted $V_{3\omega}$, which can be expressed in the following form:

$$V_{3\omega} = \frac{R_0 I_0 \alpha_R \Delta T_0}{2}, \quad (5)$$

where $R_0$ is the resistance of the metal line 4 at ambient temperature, and $\Delta T_0$ is the amplitude of the generated thermal wave.

It is then possible to determine the value of the coefficient of thermal conductivity $\lambda_F$ of the sample 8 by relating the thermal amplitude $\Delta T_0$ with the thermal conductivity of the sample 8, provided that some assumptions, set forth below, are necessarily observed.

The depth of penetration $1/q_S$ of the thermal wave (referenced 6 in FIG. 1) into the substrate 2 is defined by the equation:

$$\left|\frac{1}{q_S}\right| = \sqrt{\frac{\lambda_S}{2\omega \rho_S c_{pS}}} \quad (6)$$

where $\lambda_S$, $\rho_S$ and $c_{pS}$ respectively correspond to the thermal conductivity, the density and the specific heat capacity of the substrate 2.

The assumptions which must necessarily be complied are:
the substrate 2 is homogeneous, isotropic and semi-infinite in depth (which amounts to saying that $1/q_S \ll d_S$ where $d_S$: thickness of the substrate 2),
the heat source formed by the metal line is lineal i.e. the width 2b of the metal line 4 is negligible compared with the depth of penetration of the thermal wave $1/q_S$ (translating as $b \ll 1/q_s$),
the material of the sample 8 allows the heat flow to pass through the sample 8 perpendicular to the plane of the layer forming the sample 8 (parallel to the plane (X,Z) illustrated in FIG. 1),
$\lambda_F \ll \lambda_S$,
the width 2b of the metal line 4 is much greater than the thickness $d_F$ of the sample 8.

The increase in temperature $\Delta T_S$ in the substrate 2 can be approached using the following formula:

$$\Delta T_S = \frac{P_l}{\pi \lambda_S} \left[ -\frac{1}{2} \ln(2\omega) + \frac{1}{2} \ln\left(\frac{\lambda_S}{\rho_S c_{pS} b^2}\right) + \ln(2) - i\frac{\pi}{4} \right] \quad (7)$$

where $P_l$ is the linear heating power density per unit length of the metal line 4.

Having regard to the assumptions mentioned previously, it can be considered that the heat flow flows one-dimensionally in the direction normal to the plane of the layer 8 of material forming the sample, and that the increase in thermal amplitude $\Delta T_F$ due to the sample is independent of the angular frequency ω and is defined by the equation:

$$\Delta T_F = \frac{1}{\lambda_F} \frac{d_F}{2b} P_l \quad (8)$$

Yet, we have $\Delta T_0 = \Delta T_S + \Delta T_F$.

By plotting the straight lines $\Delta T_0$ and $\text{Re}(\Delta T_S)$ and by measuring the difference along the ordinate between these two straight lines which corresponds to $\Delta T_F$, using equation (8) it is possible to determine the value of the thermal conductivity $\lambda_F$ of the sample.

If the sample 8 is a thin film composed of an electrically conductive material, an electrically insulating film e.g. composed of $SiO_2$ and of known thickness is inter-positioned to prevent any electric short circuit between the metal line 4 and the sample 8.

Taking into account the assumptions needed for implementing the 3ω method, it can be seen that this method is not at all suited when the sample 8 is a layer that is too thin or too thick, or if it is composed of a material having strong thermal conductivity and/or having priority conductivity over the plane of the layer (thermal anisotropy).

With a thin anisotropic film, the actual flow of heat through the film is not one-dimensional and normal to the plane of the layer forming the sample, but also diffuses laterally in the sample 8 (parallel to the axis x illustrated in FIG. 1), in the regions of the sample 8 which are not covered by the metal wire 4. Therefore, as shown in the document <<Data reduction in 3 omega method for thin-film thermal conductivity determination>> by T. Borca-Tasciuc et al., Review of Scientific Instruments, vol. 72, April 2001, pages 2139-2147, for a sample in the form of a thin anisotropic layer and arranged on a semi-infinite isotropic substrate, and assuming $1/q_F \gg d_F$, the variation in temperature due to the film is expressed by the equation:

$$T_F = \frac{1}{\lambda_{Fy}} \frac{d_F}{2b} P_l CS \quad (9)$$

where C: contrast factor of thermal conductivity between the sample and the substrate, and S: effect of lateral dispersion of the heat, such that:

$$C = 1 - \frac{\lambda_{Fx}\lambda_{Fy}}{\lambda_S^2} \quad (10)$$

$$S = \frac{2}{\pi} \int_0^\infty \frac{\sin^2(\lambda)}{\lambda^3} \frac{th(\lambda\beta_F)}{\left[1 + \frac{\sqrt{k_{Fx}k_{Fy}}}{k_S} - th(\lambda\beta_F)\right]\beta_F} d\lambda \quad (11)$$

$$\beta_F = \sqrt{\frac{\lambda_{Fx}}{\lambda_{Fy}}} \frac{d_F}{b} \quad (12)$$

$k_{Fx,y}$ representing the spatial angular frequency of the thermal wave in the sample along the axis x or y respectively, $\lambda_{Fx,y}$ representing the thermal conductivity of the sample along axis x or y respectively, and λ being an integration variable.

It can therefore be seen that the theoretical model of the one-dimensional transfer of heat is only valid when C and S both tend towards 1, C tending towards 1 being equivalent to the assumption $\lambda_F \ll \lambda_S$ and S tending towards 1 being equivalent to the assumption $\beta_F \ll 1$.

If $T_F^{1D}$ is the expression of $T_F$ when the assumptions of the one-dimensional flow of heat are complied, then:

$$T_F^{1D} = \frac{1}{\lambda_{Fy}} \frac{d_F}{2b} P_l \quad (13)$$

$$T_F = CST_F^{1D} \quad (14)$$

The variation in temperature through the anisotropic film as measured using the 3ω method is therefore under-estimated by a factor (1-CS).

It is shown in document <<Data reduction in 3 omega method for thin-film thermal conductivity determination>> by T. Borca-Tasciuc et al., Review of Scientific Instruments, vol. 72, April 2001, pages 2139-2147, that the approximations of semi-infinite substrate and of linear source can be used with an error of less than 1% on measurement results if:

$$5b < \frac{1}{q_s} < \frac{d_S}{5} \quad (15)$$

One way of observing this dual inequality (15) for a given b is to act on the angular frequency ω (which is involved in the calculation of $1/q_s$).

This is possible for as long as $b < d_s/25$ (i.e. about 20 μm for a standard silicon substrate).

If not, there is no longer any frequency which allows this inequality to be observed. However, it can be seen that it is not possible to increase the value of b beyond this limit so as to reduce the value of the term $\beta_F$ and hence to increase the value of S. And the higher the value of b, the more the range of the angular frequency ω is reduced (for example when b=15 μm, the frequency corresponding to the angular frequency ω must lie within around 600 and 1000 Hz, whereas if b=1 μm, it is possible to use a frequency ranging up to 10000 Hz).

Another major limitation is related to the fact that $T_F$ is inversely proportional to b. An increase in b therefore implies a reduction in $T_F$, which may lead to a signal that is difficult to measure for films that are good heat conductors.

Similar to parameter b, it is difficult to reduce the value of the parameter $d_F$ in order to reduce the value of the term $\beta_F$ (and hence increase the value of S) since this decrease indirectly increases the measurement error inherent in the one-dimensional model through weakening of the 3ω signal.

DISCLOSURE OF THE INVENTION

It is one objective of the present invention to propose a method for the thermal characterization of a portion of material that does not have the disadvantages of the prior art i.e. which allows measurement of the thermal conductivity of a very thin or very thick portion and/or possibly having high anisotropy and/or is composed of a material with strong thermal conductivity.

For this purpose, a method is proposed for thermally characterizing a portion of at least one first material of elongate shape on which at least one portion of at least one second electrically conductive material is arranged of elongate shape, the method comprising at least the steps of:

a) determining the characteristic R(T) of the portion of the second electrically conductive material, corresponding to the variation in electrical resistance R of the portion of the second electrically conductive material as a function of the temperature T of the portion of the second electrically conductive material, b) applying an electric current of angular frequency ω between ends of the portion of second electrically conductive material and measuring the 3ω angular frequency harmonic of the electric voltage between these ends for different values of ω, c) calculating the coefficient of thermal conductivity of the portion of first material from the values of the measured 3ω angular frequency harmonic and the characteristic R(T), a width of the portion of the first material being between about 0.9 L and 1.1 L, where L: width of the portion of the second electrically conductive material.

The portion of the first material is surrounded by at least one matter thermally insulating the portion of the first material.

With this method, it is therefore possible to apply the principle of the 3ω method to ranges of materials which have a CS value different from 1, for example materials whose thermal conductivity and/or anisotropy are too high making them incompatible with the conventional, prior art 3ω method, such as germanium for example whose coefficient of thermal conductivity is about 60 W/m/K, or titanium whose coefficient of thermal conductivity is about 46 W/m/K, or platinum having a coefficient of thermal conductivity of about 72 W/m/K, and/or portions of materials whose thickness, too thin or too thick in comparison with conductivities, are incompatible with the implementation of the conventional, prior art 3ω method.

For materials that are compatible with the prior art 3ω method, this method makes it possible to improve the precision of thermal conductivity measurement, since the heat flow passing through the portion of the first material is one-dimensional, i.e. oriented in one same direction (in the direction of the thickness of the portion of the first material) over the entire volume of the portion of the first material, contrary to the flow passing through a layer composed of the first material, and it is sufficient for example to reduce the width 2b to obtain a measurable signal without excessive error. This one-dimensional nature of the heat flow passing through the portion of the first material over its entire thickness is also obtained by means of the fact that the portion of first material is surrounded by at least one matter forming thermal insulation of the portion of the first material i.e. preventing lateral dispersion of the heat emitted by the portion of second material around the portion of first material.

The portions of the first and of the second material are of elongate shape i.e. a shape whose length is greater than the width, for example such that the length is about 10 times greater than the width. This elongate shape may correspond to a rectangular parallelepiped for example, a wire, a cylinder or more generally a substantially rectilinear shape of uniform width.

The thickness of the portion of the second electrically conductive material may be equal to or less than about 0.1. L, and/or the length of the portion of the second electrically conductive material may be equal to or more than about 10. L.

The length of the portion of the first material may be equal to or more than about 10 times the width of the portion of the first material, and/or the thickness of the portion of the first material may be less than the depth of penetration of a heat flow generated at step b) in the portion of the first material, the heat flow reaching the substrate which can then be considered to be a heat sink.

The portion of the first material and/or the portion of the second electrically conductive material may be of substantially rectangular parallelepiped shape.

The portion of the first material may be arranged between the portion of the second electrically conductive material and a substrate, the substrate possibly being composed of at least one semiconductor.

In addition, the substrate may have a thickness equal to or more than about 10 times the penetration depth of a heat flow generated at step b) in the substrate and/or a width equal to or more than about 10 times the width of the portion of the first material.

The second electrically conductive material may be a metal.

If the first material is electrically conductive, a portion of a dielectric material may be arranged between the portion of first material and the portion of the second electrically conductive material, which allows the electrical insulating of the portion of first material from the portion of the second electrically conductive material.

The calculation of the coefficient of thermal conductivity of the portion of first material may comprise at least the steps of:

calculating a temperature coefficient of resistance $\alpha_R$ of the portion of the second electrically conductive material such that $$\alpha_R = \frac{1}{R} \cdot \frac{dR(T)}{R},$$

calculating an amplitude of the thermal wave $\Delta T_0$ generated by the electric current of angular frequency ω such that $$\Delta T_0 = \frac{2V_{3\omega}}{R_0 I_0 \alpha_R},$$

where $V_{3\omega}$ is the 3ω angular frequency harmonic of the electric voltage between the ends of the portion of the second electrically conductive material, $R_0$ is the electrical resistance of the portion of the second electrically conductive material at ambient temperature, and $I_0$ is the amplitude of the electric current of angular frequency ω, calculating an increase in temperature $\Delta T_S$ in a substrate, such that the portion of the first material is arranged between the portion of the second electrically conductive material and the substrate, as per the equation $$\Delta T_S = \frac{P_l}{\pi \lambda_S}\left[-\frac{1}{2}\ln(2\omega) + \frac{1}{2}\ln\left(\frac{\lambda_S}{\rho_S c_{pS} b^2}\right) + \ln(2) - i\frac{\pi}{4}\right],$$

where $P_l$ is the heating power per unit of length of the portion of the second electrically conductive material, $\lambda_S$ is the coefficient of thermal conductivity of the substrate, $\rho_S$ is the density of the substrate, $c_{pS}$ is the specific heat capacity of the substrate, and 2b is the width of the portion of the second electrically conductive material, calculating the coefficient of thermal conductivity $\lambda_F$ of the portion of the first material such that $$\lambda_F = \frac{d_F}{\Delta T_F 2b} P_l,$$

where $d_F$ is the thickness of the portion of the first material, and $\Delta T_F = \Delta T_0 - \Delta T_S$.

The portions of the first and second material may be prepared by implementing the following steps:

depositing a layer composed of the first material on a substrate, depositing a layer composed of the second electrically conductive material on the layer composed of the first material, forming an etching mask of elongate pattern, photolithography and etching of the layers composed of the first and second materials according to the pattern of the etching mask, forming the portion of the first material and the portion of the second electrically conductive material, removing the etching mask.

If the first material is electrically conductive, a layer composed of a dielectric material may be deposited on the layer composed of the first material, the layer composed of the second electrically conductive material then being deposited on the layer composed of dielectric material, the layer composed of dielectric material also able to be etched according to the pattern of the etching mask.

The value of the coefficient of thermal conductivity of the matter surrounding the portion of the first material may be equal to or lower than about one tenth of the value of the thermal conductivity coefficient of the portion of first material.

In another variant, the value of the coefficient of thermal conductivity of the matter surrounding the portion of the first material may be equal to or lower than the value of the thermal conductivity coefficient of the portion of first material, and a thickness of the matter surrounding the portion of the first material may be equal to or less than about one tenth of a thickness of the portion of the first material.

BRIEF DESCRIPTION OF THE DRAWINGS

The present invention will be better understood on reading the description of examples of embodiment given solely as illustrations that are in no way limiting, with reference to the appended drawings in which.

Identical, similar or equivalent parts in the different figures described below carry the same reference numbers to facilitate cross-reading between the figures.

The different parts illustrated in the figures are not necessarily drawn to scale for better legibility of the figures.

The different possibilities (variants and embodiments) are to be construed as not being exclusive of each other and may be combined together.

DETAILED DESCRIPTION OF PARTICULAR EMBODIMENTS

Figure 1:
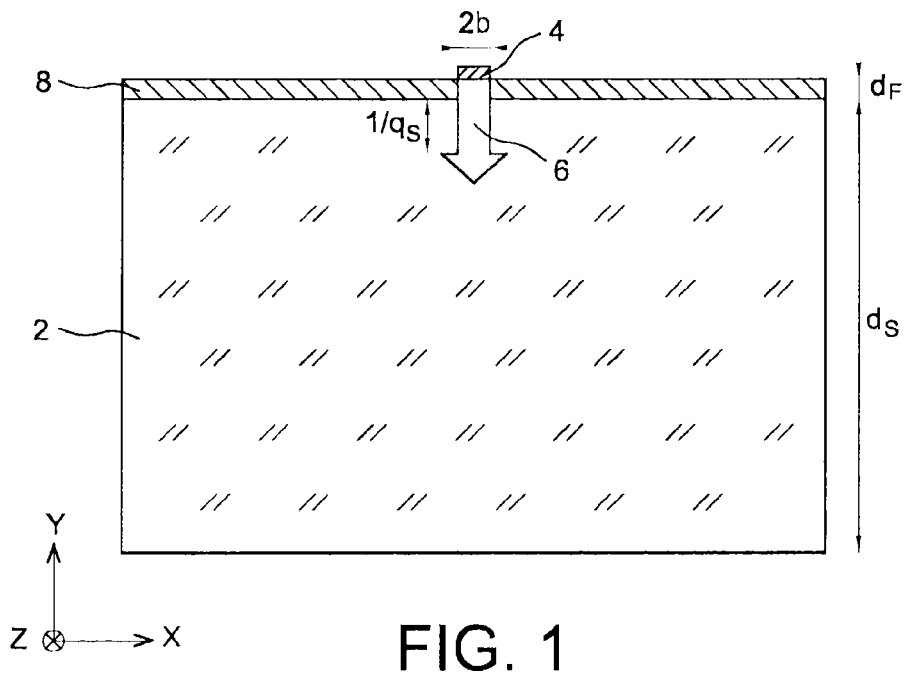
FIG. 1 is a cross-sectional view of a test structure used when implementing a method for measuring the thermal conductivity of a thin layer of material, according to the 3ω method of the prior art, FIGS. 2A, 2B and 3 respectively illustrate cross-sectional and overhead views of a test structure used when implementing a method for the thermal characterization of a portion of material according to one particular embodiment of the invention.
Figure 2A:
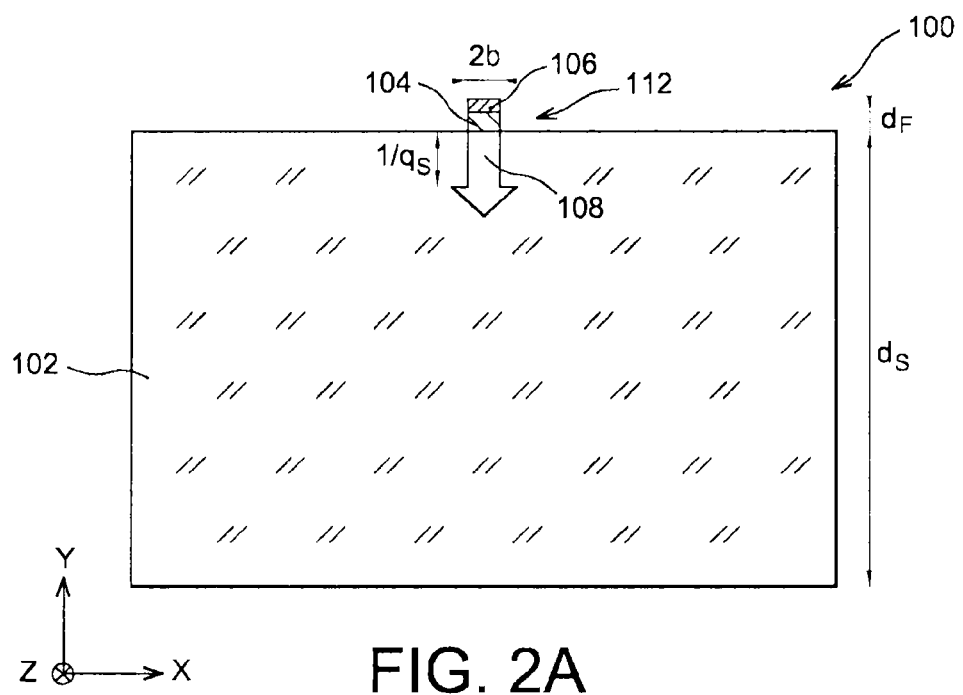

With reference firstly to FIG. 2A which illustrates an example of a test structure 100 used when implementing a method for the thermal characterization of a portion of material 104 according to one particular embodiment.

The test structure 100 comprises a substrate 102, here composed of silicon and of thickness $d_S$ of between about 100 μm and 1 cm for example, on which a portion 104 of thickness $d_F$ e.g. between about 100 nm and 10 μm is deposited, whose thermal conductivity it is sought to measure.

A portion 106 composed of an electrically conductive material such as a metal e.g. aluminium and/or nickel and/or gold, of uniform width (dimension along the x axis illustrated in FIG. 2A) equal to $2b$ (b therefore corresponding to one half of the width of the portion 106), is placed on the portion 104 whose thermal conductivity is to be measured. The portions 104 and 106 are both of elongate shape i.e. having a length (dimension along the Z axis perpendicular to the x axis and illustrated in FIG. 2A) greater than at least 10 times their width. The width $2b$ is between about 1 μm and 30 μm for example, and the length of the portions 104 and 106 is between about 10 μm and 1 cm for example.

Contrary to the conventional 3ω method in the prior art, the material whose thermal conductivity it is sought to measure is not in the form of a thin layer but in the form of a portion 104 which here has a width (dimension along axis x) equal to $2b$, i.e. equal to the width of the portion 106. The portion 106 therefore forms a metal line arranged on the portion 104 which shall be called the <<sample>>. The metal line 106 and the sample 104 therefore form a structure of mesa type, the shape of the sample 104 in a plane parallel to plane (X, Z) in FIG. 2A (plane parallel to the face of the substrate 102 on which the sample 104 and the metal line 106 are formed) being substantially similar to the shape of the metal line 106 along this same plane.

Therefore, by forming the sample 104 such that its width is substantially equal to the width of the metal line 106, the lateral dispersion of the heat emitted by the metal line 106 is blocked, irrespective of the physical properties of the sample 104, i.e. irrespective of its thickness or type of material. In addition, the blocking of this lateral dispersion of the heat emitted by the metal line 106 is also obtained by means of the fact that the portion 104 is surrounded by matter 112 forming thermal insulation around this portion 104. In the case in hand, the value of coefficient of thermal conductivity of this matter 112, in this case air, is equal to or less than about one tenth of the value of the thermal conductivity coefficient of the portion 104. Therefore, the air 112 surrounding the sample 104 forms excellent thermal insulation. As illustrated in FIG. 2A, a heat flow 108 created by the metal line 106 and passing through the sample 104 is therefore indeed one-dimensional and is directed in a single direction perpendicular to the face of the substrate 102 on which the sample 104 and the metal line 106 are formed (direction parallel to the axis y illustrated in FIG. 2A).

Figure 3:
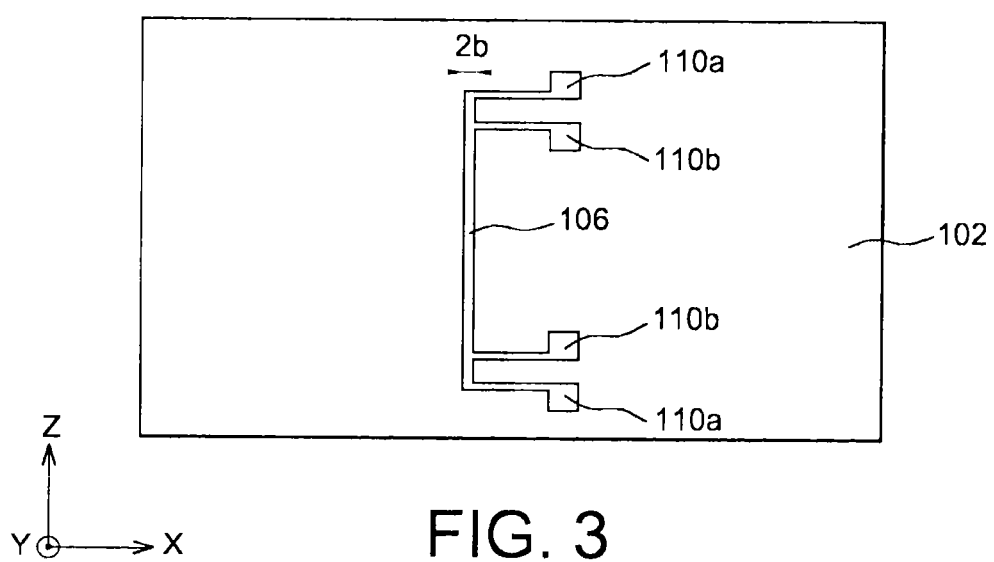

The test structure 100 is also illustrated in FIG. 3 from overhead. In this figure, it can be seen that four electric contacts 110a, 110b are electrically connected to the ends of the metal line 106. The contacts 110a will subsequently be used to cause a current to circulate in the metal line 106, whilst the contacts 110b will be used to measure a voltage at the terminals of the metal line 106. The thickness of the metal line 106 is between about 100 nm and 1 μm for example, and is 400 nm for example. This thickness is particularly chosen to be sufficiently thick so that, when the contacts 110a, 110b are made from the same layer of material as the layer used to form the metal line 106, it is possible to form electric contacts with the apparatus intended to circulate the current in the metal line 106 and to measure the voltage at the terminals of the metal line 106, this thickness also being sufficiently thin so that heat is not stored in the metal line 106 and/or the contacts 110a, 110b when a current is caused to circulate in the metal line 106. In general, the test structure 100 can be prepared in accordance with one of the different possible configurations allowing the application of a measuring method of <<four-point>> type or <<Van der Pauw>> type.

Assuming that $d_F \ll 1/q_F$, the sample 104 acts as a thermal resistance such that:

$$R_F = \frac{1}{\lambda_{F_y}} \frac{d_F}{2b} \tag{16}$$

It can therefore be seen that the lower the value of b, the higher the value of $R_F$ and hence also of $T_F$. Therefore the width $2b$ is chosen to be the narrowest possible in order to have the highest possible value of $T_F$, which allows a reduction in the error of value $T_F$, and hence also of the thermal conductivity $\lambda_F$.

If the sample 104 is composed of an electrically conductive material, between the metal line 106 and the sample 104, a portion of a dielectric material is inserted e.g. composed of $SiO_2$, allowing a short circuit to be prevented between the metal line 106 and the sample 104. The cross-section, in a plane parallel to the plane (X, Z) illustrated in FIG. 3, of this portion of dielectric material is similar for example to the cross-section of the sample 104 and/or of the metal line 106 along this same plane.

Such test structure 100 is obtained firstly by depositing, on the substrate 102, a layer composed of the material intended to form the sample 104, then depositing a dielectric layer if the sample 104 is composed of an electrically conductive material, followed by the depositing of a layer composed of the electrically conductive material intended to form the metal line 106. An etching mask e.g. composed of resin, is formed on the layer composed of electrically conductive material.

The pattern of the etching mask corresponds for example to the pattern of the metal line 106 and of the contacts 110a, 110b illustrated in FIG. 3. The different layers previously deposited on the substrate 102 are then etched following the pattern of the etching mask, forming the sample 104 and the metal line 106 and the contacts 110a, 110b. The etching mask is then removed.

Since it may be difficult to stop etching just level with the surface of the substrate 102, it is possible to allow slight etching of the substrate 102 insofar as this depth remains small compared with the depth of penetration of the heat flow 108 in the substrate 102, and insofar as the contribution of this remaining volume of the substrate, arranged underneath the sample 104, towards the measured signal remains negligible compared with the signal due to the sample 104.

The matter 112 surrounding the portion 104 may be a vacuum or a gas such as air, an inert gas (nitrogen, argon, helium, . . . ), or a solid composed of plastics, rubber, epoxy, polystyrene, or any other material whose coefficient of thermal conductivity is equal to or lower than about one tenth of the value of the thermal conductivity coefficient of the portion of first material.

Figure 2B:
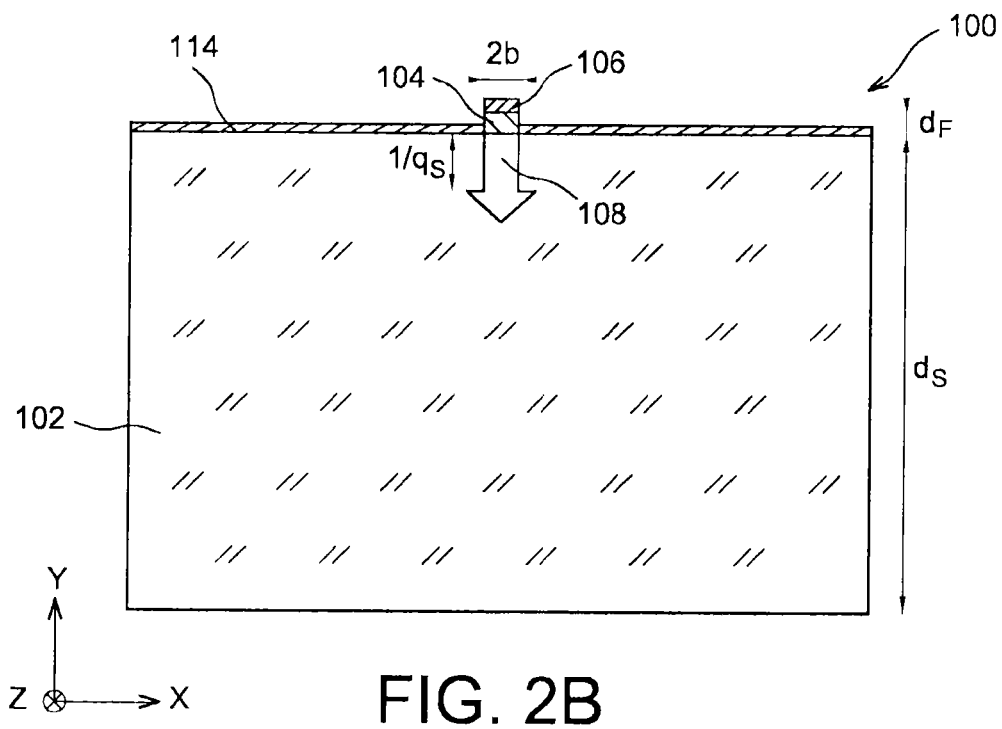

Another variant of embodiment of the test structure 100 is illustrated in FIG. 2B. In this figure, the portion 104 is surrounded by matter 114 whose coefficient of thermal conductivity is equal to or lower than the value of the thermal conductivity coefficient of the portion 104 of first material. In addition, the thickness (dimension along axis y illustrated in FIG. 2B) of the matter 114 surrounding the portion 104 is equal to or less than about one tenth of the thickness (dimension along axis y) of the portion 104. In the example in FIG. 2B, the matter 114 partly surrounding the portion 104 is in the form of a layer of silicon or silicon nitride. With said matter 114 meeting these conditions of thickness and coefficient of thermal conductivity, a heat flow 108 also passes through the portion 104 that is substantially one-dimensional throughout the portion 104. The remainder of the portion 104 is surrounded for example by matter forming thermal insulation e.g. air.

Using the test structure 100, a method is implemented for the thermal characterization of the sample 104 based on the principle of the 3ω method.

The instruments used for implementing this method are similar to those described in the document <<Thermal conductivity measurement from 30 to 750 K: the 3 omega method>> by D. G. Cahill, Rev. Sci. Instrum. 61(2), February 1990, pages 802-808.

Therefore, to determine the thermal conductivity of the sample 104, first the electrical resistance of the metal line 106 is measured at the different temperatures to which the test structure 100 is subjected. From these measurements it is possible to obtain the characteristic R(T) of the metal line 106.

An electric current i(t) is then applied of angular frequency ω and amplitude $I_0$ ($i(t)=I_0 \cdot \cos(\omega t)$) to the metal line 106 via the contacts 110a, and the 3ω angular frequency harmonic of the electric voltage, denoted $V_{3\omega}$, is measured at the terminals of the metal line 106, i.e. between the contacts 110b, for different values of ω.

Using the values of the previously measured 3ω angular frequency harmonic, and of the characteristic R(T) of the metal line 106, the value of the coefficient of thermal conductivity of the portion 104 is then calculated. An example is given below for performing this calculation.

First the temperature coefficient of resistance $\alpha_R$ of the metal line 106 is calculated using the equation $$\alpha_R = \frac{1}{R} \cdot \frac{dR(T)}{R},$$

and the amplitude of the thermal wave $\Delta T_0$ generated by the current i(t) such that $$\Delta T_0 = \frac{2V_{3\omega}}{R_0 I_0 \alpha_R},$$

where $R_0$ is the electrical resistance of the metal line 106 at ambient temperature.

Next the increase in temperature $\Delta T_S$ in the substrate 102 is calculated using the equation $$\Delta T_S = \frac{P_l}{\pi \lambda_S}\left[-\frac{1}{2}\ln(2\omega) + \frac{1}{2}\ln\left(\frac{\lambda_S}{\rho_S c_{pS} b^2}\right) + \ln(2) - i\frac{\pi}{4}\right],$$

where $P_l$ is the heating power per unit of length of the metal line 106, $\lambda_S$ is the coefficient of thermal conductivity of the substrate 102, $\rho_S$ is the density of the substrate 102, and $c_{pS}$ is the specific heat capacity of the substrate 102.

Next the straight lines $Re(\Delta T_S)$ and $\Delta T_0$ are plotted in relation to $\ln(2\omega)$. Since $\Delta T_F = \Delta T_0 - \Delta T_S$, the difference is measured along the ordinate between these two straight lines, which allows the calculation of the coefficient of thermal conductivity $\lambda_F$ of the sample 104 such that $$\lambda_F = \frac{d_F}{\Delta T_F 2b} P_l.$$

The method of the invention therefore allows the thermal characterization of an entire range of materials which cannot be characterized using the prior art 3ω method, for example very thin or very thick portions, having high anisotropy or very good thermal conductivity. In addition, for materials which can be thermally characterized using the conventional prior art 3ω method, this method allows improved precision of measurement of the thermal conductivity of these materials.

A comparison is given below of the results obtained between measurement of the thermal conductivity of a material having strong thermal conductivity in the form of a sample similar to sample 104 (i.e. in the form of a portion of elongate shape of width equal to 2b) and measurement of the thermal conductivity of this same material in the form of a thin layer using the conventional, prior art 3ω method.

The sample and the thin layer were arranged in two separate test structures, each comprising a substrate of silicon with the following characteristics:

$\rho_S$=2330 kg/m³
$c_{pS}$=710 J/kg/K
$\lambda_S$=150 W/m/K
$d_S$=525 μm

The thermal conductivity and the thickness of the sample and of the thin layer were respectively 30 W/m/K and 1 μm. The metal line was similar on both test structures. Finally, the applied linear power is 30 W/m.

The values are given below of the variations in temperature measured on the sample ($T_{F1D}$) and the thin layer ($T_{Flayer}$) for different values of b:

| b (μm) | $T_{F1D}$ (° C.) | $T_{Flayer}$ (° C.) |
| --- | --- | --- |
| 1 | 0.5 | 0.32 |
| 5 | 0.1 | 0.087 |
| 10 | 0.05 | 0.045 |
| 15 | 0.03 | 0.028 |

From the above results it can be seen that for a metal line of width equal to 2 μm, the measured value of $T_{Flayer}$ for the thin layer differs by about 57% from the value $T_{F1D}$ obtained for the sample, $T_{F1D}$ being the value allowing the true value to be found of the thermal conductivity of the tested material which is 30 W/m/K.

This difference in value is notably due to strong dispersion of heat occurring in the thin layer due to the strong thermal conductivity of the material (30 W/m/K). It can also be seen that by increasing the width of the metal line, the difference between the measured values $T_{Flayer}$ and $T_{F1D}$ is decreased. However, this increase in the width of the metal line leads to a drop in the temperature to be measured, which then becomes difficult to measure thereby increasing the probability of measurement error.

Similarly, a comparison is given below of the results obtained for a highly anisotropic material in the form of a sample similar to sample 104, and the measurement of the thermal conductivity of this same material in the form of a thin layer using the prior art 3ω method.

The silicon substrate used is similar to the one described previously. The thermal conductivity of the material forming the thin layer and the sample is: $\lambda_{FX}$=50 W/m/K and $\lambda_{FY}$=10 W/m/K.

The thickness of the thin layer and of the sample is 1 μm. The applied linear power is 30 W/m.

The values of the variations in temperature measured for the sample ($T_{F1D}$) and the thin layer ($T_{Flayer}$) at different values of b are:

| b (μm) | $T_{F1D}$ (° C.) | $T_{Flayer}$ (° C.) |
| --- | --- | --- |
| 1 | 1.5 | 0.707 |
| 5 | 0.3 | 0.244 |
| 10 | 0.15 | 0.133 |
| 15 | 0.1 | 0.091 |

For the value of b=1 μm, an even greater difference is observed (112%) between the measured values of $T_{F1D}$ and $T_{Flayer}$. By increasing the width of the metal line, the difference between the measured values $T_{F1D}$ and $T_{Flayer}$ is reduced but this increase in the width of the metal leads to a temperature drop, which again raises problems.

In addition, when the sample and the thin layer do not have a thickness of 1 μm but of 3 μm, the following values were obtained:

| b (μm) | $T_{F1D}$ (° C.) | $T_{Flayer}$ (° C.) |
| --- | --- | --- |
| 1 | 1.5 | 0.365 |
| 5 | 0.3 | 0.179 |
| 10 | 0.15 | 0.112 |
| 15 | 0.1 | 0.081 |

It can therefore be seen that the phenomenon of dispersion between the values is aggravated when the thickness of the material whose thermal conductivity is being measured is increased.

The different comparisons carried out above clearly illustrate the advantages of the invention compared with the prior art 3ω method, i.e. the ability to perform precise measurement of the thermal conductivity of a portion that is very thin or very thick and/or possibly having high anisotropy and/or composed of a material having strong thermal conductivity.

The invention claimed is:

1. A method for thermal characterization of a portion of at least one first material of elongate shape on which there is arranged at least one portion of at least one second electrically conductive material of elongate shape, the method comprising:
  a) determining a characteristic R(T) of the portion of the second electrically conductive material corresponding to a variation in electrical resistance R of the portion of the second electrically conductive material as a function of temperature T of the portion of the second electrically conductive material;
  b) applying an electric current of angular frequency ω between ends of the portion of the second electrically conductive material and measuring 3 ωangular frequency harmonic of the electric voltage between these ends for different values of ω;
  c) calculating a coefficient of thermal conductivity of the portion of the first material from the values of the measured 3ω angular frequency harmonic and the characteristic R(T);
  a width of the portion of the first material being between about 0.9 L and 1.1 L, wherein L is the width of the portion of the second electrically conductive material, and wherein the portion of the first material is surrounded by at least one matter thermally insulating the portion of the first material,
  wherein the portions of the first and second material are prepared by implementing:
  depositing a layer composed of the first material on a substrate;

depositing a layer composed of the second electrically conductive material on the layer composed of the first material;

forming an etching mask having a pattern of elongate shape;

photolithography and etching the layers composed of the first and second materials according to the pattern of the etching mask, forming the portion of the first material and the portion of the second electrically conductive material;

removing the mask.

2. The method according to claim 1, wherein the thickness of the portion of the second electrically conductive material is equal to or less than about 0.1 L, and/or the length of the portion of the second electrically conductive material is equal to or greater than about 10 L.

3. The method according to claim 1, wherein the length of the portion of the first material is equal to or greater than about 10 times the width of the portion of the first material, and/or the thickness of the portion of the first material is smaller than the depth of penetration of a heat flow generated into the portion of the first material during applying b).

4. The method according to claim 1, wherein the portion of the first material and/or the portion of the second electrically conductive material are in a shape of a substantially rectangular parallelepiped.

5. The method according to claim 1, wherein the second electrically conductive material is a metal.

6. The method according to claim 1, wherein if the first material is electrically conductive, a portion of a dielectric material is arranged between the portion of the first material and the portion of the second electrically conductive material.

7. The method according to claim 1, wherein the calculation of the coefficient of thermal conductivity of the portion of the first material comprises:

calculating a temperature coefficient of resistance $\alpha_R$ of the portion of the second electrically conductive material such that $$\alpha_R = \frac{1}{R} \cdot \frac{dR(T)}{R};$$

calculating an amplitude of the thermal wave $\Delta T_0$ generated by the electric current of angular frequency $\omega$ such that $$\Delta T_0 = \frac{2 V_{3\omega}}{R_0 I_0 \alpha_R},$$

wherein $V_{3\omega}$ is the 3ω angular frequency harmonic of the electric voltage between the ends of the portion of the second electrically conductive material, $R_0$ is the electrical resistance of the portion of the second electrically conductive material at ambient temperature, and $I_0$ is the amplitude of the electric current of angular frequency δ;

calculating an increase in temperature $\Delta T_S$ in the substrate, such that the portion of the first material is arranged between the portion of the second electrically conductive material and the substrate, as per the equation $$\Delta T_S = \frac{P_l}{\pi \lambda_S}\left[-\frac{1}{2}\ln(2\omega) + \frac{1}{2}\ln\left(\frac{\lambda_S}{\rho_S c_{pS} b^2}\right) + \ln(2) - i\frac{\pi}{4}\right],$$

wherein $P_l$ is the heating power per unit of length of the portion of the second electrically conductive material, $\lambda_S$ is the coefficient of thermal conductivity of the substrate, $\rho_S$ is the density of the substrate, $c_{pS}$ is the specific heat capacity of the substrate, and 2b the width of the portion of the second electrically conductive material;

calculating the coefficient of thermal conductivity $\lambda_F$ of the portion of the first material such that $$\lambda_F = \frac{d_F}{\Delta T_F 2b} P_l,$$

where $d_F$ is the thickness of the portion of the first material, and $\Delta T_F = \Delta T_0 - \Delta T_S$.

8. The method according to claim 1, wherein, if the first material is electrically conductive, a layer composed of a dielectric material is deposited on the layer composed of the first material, the layer composed of the second electrically conductive material then being deposited on the layer composed of dielectric material, the layer composed of dielectric material also being etched following the pattern of the etching mask.

9. The method according to claim 1, wherein the value of the coefficient of thermal conductivity of the matter surrounding the portion of the first material is equal to or less than about one tenth of the value of the thermal conductivity coefficient of the portion of the first material.

10. The method according to claim 1, wherein the value of the coefficient of thermal conductivity of the matter surrounding the portion of the first material is equal to or lower than the value of the thermal conductivity coefficient of the portion of the first material, and wherein a thickness of the matter surrounding the portion of the first material is equal to or less than about one tenth of a thickness of the portion of the first material.

11. The method according to claim 1, wherein the portion of the first material is arranged between the portion of the second electrically conductive material and the substrate.

12. The method according to claim 11, wherein the substrate has a thickness equal to or more than about 10 times the depth of penetration of a heat flow generated into the substrate during the applying b) and/or a width equal to or more than about 10 times the width of the portion of the first material.

* * * * *